Aug. 24, 1965 F. W. ANDERSON Plant Pat. 2,548
ALMOND TREE
Filed April 20, 1964
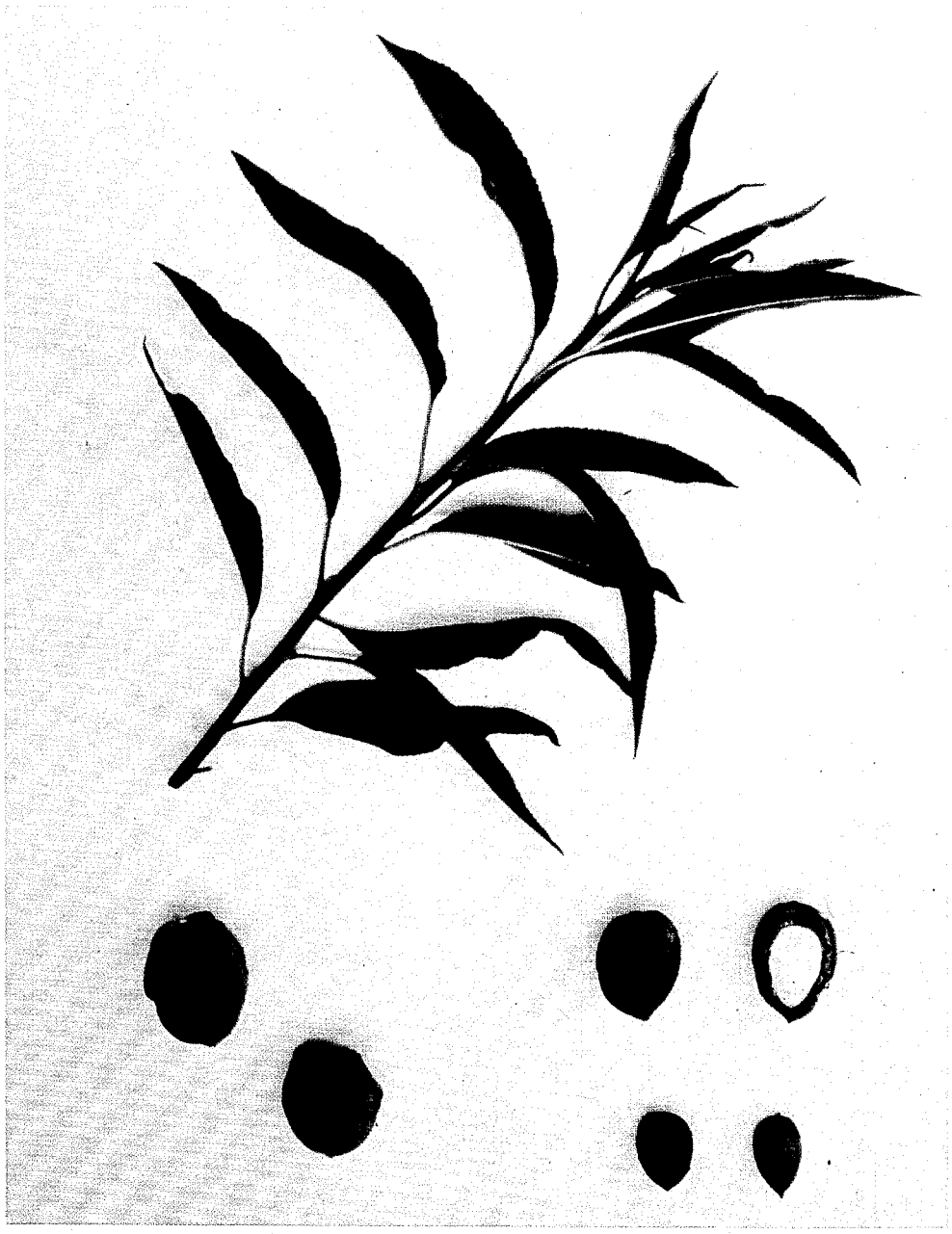
INVENTOR
*Frederic W. Anderson*
*Webster & Webster*
ATTYS.

United States Patent Office

Plant Pat. 2,548
Patented Aug. 24, 1965

2,548
ALMOND TREE

Frederic W. Anderson, Merced, Calif., assignor to Arthur Bright, Le Grand, Calif.

Filed Apr. 20, 1964, Ser. No. 361,318
1 Claim. (Cl. Plt.—30)

This invention relates to a new and distinct variety of almond tree which is a regular and very productive bearer of nuts well distributed on the tree, and which nuts, including the kernels, are particularly characterized—as to novelty—by an improved shape and appearance in comparison to the Mission (unpatented); the latter being second only to the Nonpareil (unpatented) in importance in California.

More particularly, both the nut and kernel of the present variety are desirably longer and thinner than the Mission.

Further, the nuts of the present variety have less than two percent doubles as compared to seven to twelve percent doubles in the Mission.

Additionally, the crop of the present variety is late in harvest in comparison to said Mission.

Another distinctive characteristic of the instant variety of almond tree is a late blooming period which is about one week later than the Mission, and which heretofore has been the latest blooming commercial variety of almond tree. Such late blooming period of the present variety is of substantial advantage in that the weather is then usually more temperate and conducive to pollination and setting of fruit. Also, there is less probability of loss from frost and rain.

The herein claimed variety of almond tree was originated by me in my experimental orchard located near Le Grand, Merced County, California, during the course of a long and continuing plant breeding program seeking improved varieties of fruits and nuts, including almonds. Such origination was accomplished as follows:

A tree of the Mission, in a block thereof, was top-worked on one-half to the Ruby (United States Plant Patent No. 1,698), and all the Ruby nuts produced during three successive seasons were gathered, planted, and the resultant seedlings grown under continuing observation; the Ruby thus having been the seed parent, and the Mission the probable pollen parent.

The present variety is one of such seedlings, and when it came into bearing I recognized its novel and distinctive characteristics and, therefore, selected it for subsequent reproduction. Thereafter, I asexually reproduced the variety in my experimental orchard, located as aforesaid, by top-working on mature orchard trees; such reproductions having run true to the parent in all respects.

The drawing comprises an illustration, by photographic reproduction in color, of a first year shoot with leaves; a pair of nuts in the hull; a nut with the hull removed; a nut with one-half of the shell removed and the kernel cut to expose the meat; a kernel from one side; and another kernel from one edge.

Referring now more specifically to the botanical details of this new and distinct variety of almond tree, the following is an outline description thereof; all major color plate identifications, by comparison with fresh specimens; being by reference to Maerz and Paul Dictionary of Color; except where common terms of color definition are employed:

Tree:
- *Density.*—Open to dense.
- *Size.*—Large to medium.
- *Vigor.*—Vigorous.

Trunk:
- *Form.*—Medium.
- *Texture.*—Medium.

Branches:
- *Form.*—Medium.
- *Texture.*—Medium.
- *Branching habit.*—Medium.

Foliage: Quantity—Medium to abundant.

Leaves:
- *Size.*—Medium. Average length—4". Average width—¾".
- *Shape.*—Oval; acutely pointed.
- *Thickness.*—Medium.
- *Texture.*—Smooth.
- *Margin.*—Glandular; crenate.
- *Petiole.*—Medium length.
- *Glands.*—Average number and position—2 on petiole. Alternate; medium size.
- *Color.*—Top side—Medium Green (23–J–6). Under side—Lighter Green (22–K–6).

Bloom:
- *Amount of bloom.*—Heavy.
- *Color.*—White.
- *Blooming period.*—Late, as compared to present commercial varieties. About one week later than Mission.

Crop:
- *Bearing.*—Regular bearer.
- *Productivity.*—Very heavy.
- *Distribution of nuts on trees.*—Well distributed.
- *Harvest period.*—Late, as compared to Mission. About one week later.
- *Tenacity.*—Hangs well on tree.

Hull:
- *Outer surface.*—Smooth.
- *Form.*—Regular.
- *Thickness.*—Thin.
- *Flesh.*—Tough.
- *Color.*—Gray-green (15–H–3) with silvery sheen.
- *Dehiscence.*—Opens freely.
- *Splitting.*—Along suture; freely at base.

Nut:
- *Size.*—Medium. Average length—1 3/16". Average thickness—¾". Average weight—2.2 grams.
- *Form.*—Length/width—ovate. Width thickness—medium to flat.
- *Shell.*—Hard; smooth. Outer shell—hard. Inner shell—hard.
- *Color.*—Medium Light Brown (13–I–8).
- *Pits.*—Small; numerous; shallow; irregular.
- *Base.*—Square.
- *Stem scar.*—Large.
- *Apex.*—Acute.
- *Wing.*—Narrow; thick.
- *Inner surface.*—Light.
- *Ventral streak.*—Dark; broad; long; point obtuse.
- *Percentage of kernel to nut on average sample.*—48 percent.

Kernel:

*Size.*—Medium. Average length—15/16". Average width—5/8". Average thickness—5/16".

*Kernels per ounce on average sample.*—28.

*Form.*—Length/width—ovate. Width thickness—medium to flat.

*Base.*—Square.

*Stem scar.*—Small.

*Apex.*—Acute.

*Surface.*—Smooth.

*Pellicle*—Thin.

*Pubescene.*—Smooth.

*Color.*—Medium Brown (14–I–11).

*Number of doubles.*—Very few; less than two percent.

*Defective kernels.*—Very few.

*Flavor.*—Sweet; normal.

*Quality.*—Good.

The tree and its nuts herein described may vary in slight detail due to climatic and soil conditions under which this variety may be grown; the present description being of the variety as grown in the Central Valley of California.

The following is claimed:

A new and distinct variety of almond tree, substantially as illustrated and described, characterized—in comparison to the Mission—by a blooming period about one week later; and by the regular and very productive bearing of later-in-harvest nuts which are longer, thinner, and with less doubles.

No references cited.

ABRAHAM G. STONE, *Primary Examiner.*